United States Patent [19]

Lagarde et al.

[11] Patent Number: 5,130,449

[45] Date of Patent: Jul. 14, 1992

[54] ISOLATION OF STEARIDONIC ACID FROM FATTY ACID MIXTURES

[75] Inventors: Michel Lagarde, Chassieu, France; Helmut Traitler, Vevey; Hans-Juergen Wille, Villeneuve, both of Switzerland

[73] Assignee: Nestec S.A., Vevey, Switzerland

[21] Appl. No.: 521,311

[22] Filed: May 9, 1990

[30] Foreign Application Priority Data

May 22, 1989 [CH] Switzerland ............... 1919/89

[51] Int. Cl.$^5$ ................................ C11B 7/00
[52] U.S. Cl. ................................ 554/186; 554/191
[58] Field of Search ............... 260/420, 425; 514/558

[56] References Cited

U.S. PATENT DOCUMENTS 4,701,468 10/1987 Mendy et al. ............... 260/406
4,776,984 10/1988 Traitler et al. ............... 260/420

OTHER PUBLICATIONS

Chemical Abstracts, Traitler et al., vol. 109, No. 6, p. 103, 1988, 39686x.
Chemical Abstracts, Wille et al., vol. 107, No. 22, p. 136, 1987, 200830k.
Chemical Abstracts, Wille et al., vol. 110, No. 8, p. 135, 1988, 59848a.
Abstract of JP 050752 (Sep. 18, 1986).
Wille, et al., "Continuous Process for the Concentration of Polyunsaturated Fatty Acids", *Fat Sci. Technol.*, 90(12), 476–481: 1988 (Translation).
Traitler et al., "Fractionation of Blackcurrant Seed Oil", *J. Am. Oil Chem. Soc.*, 65(5) 755–760: 1988.
Wille, et al., "Production of Polyenoic Fish Oil Fatty Acids by Combined Urea Fractionation and Industrial Scale Preparative HPLC", *Rev. Fr. Corps. Gras.*, 34(2) 69–74: 1987.

*Primary Examiner*—Jose G. Dees
*Assistant Examiner*—Deboroh D. Carr
*Attorney, Agent, or Firm*—Vogt & O'Donnell

[57] ABSTRACT

Substantially pure stearidonic acid is isolated from a mixture of polyunsaturated fatty acids by fractionating at 25% to 35% by weight solution of fatty acids by high-performance reverse-phase liquid chromatography using a mobile phase of 75% to 95% by weight methanol and 25% to 5% by weight water. The isolated stearidonic acid is used to prepare pharmaceutical compositions which are administered to treat cardiovascular and thrombo-embolic diseases associated with platelet aggregation.

20 Claims, No Drawings

ISOLATION OF STEARIDONIC ACID FROM FATTY ACID MIXTURES

BACKGROUND OF THE INVENTION

This invention relates to the production of stearidonic acid from a mixture of fatty acids in which it is present as a minor constituent.

It is known that essential fatty acids of the n-3 series (nomenclature defined by the position of the first double bond from the methyl group) lead by a chain reaction to series 3 prostaglandins which inhibit the aggregation of blood platelets.

The first element of this chain is α-linolenic acid (ALA, C 18:3 Δ9,12,15) of which the conversion into stearidonic acid (SA, C 18:4 Δ6,9,12,15) is attributable to the activity of the enzyme Δ6 desaturase which is shown to weaken with age and as a result of certain diseases. The synthesis of the series 3 prostaglandins is thus compromised. To overcome this weakness of the organism, it is proposed to introduce stearidonic acid directly into the body.

Japanese patent application 86 050 752 relates to a process for the separation of stearidonic acid from fish oil which comprises the steps of converting the fatty acids present therein into their ethyl esters, treating the ethyl esters by molecular distillation and collecting the head fraction, reacting it with urea in methanol, collecting the unreacted fraction and, finally, separating a fraction enriched with ethyl ester from the stearidonic acid by two successive operations of reverse-phase partition chromatography.

A purity of 85% by weight is thus obtained for a yield of 1.8%, based on the oil used, which represents a recovery of 48% of the stearidonic acid present in the starting material.

In addition, European patent 178 442 relates to the enrichment of blackcurrant seed oil with γ-linolenic acid (GLA, C 18:3 Δ6,9,12) by the double complexing with urea of a mixture of fatty acids eminating from the saponification of blackcurrant oil, followed by high-performance reversephase liquid chromatography. According to this patent, separation appeared particularly difficult, enrichment of the mixture only appearing possible in regard to its major constituent, γ-linolenic acid.

SUMMARY OF THE INVENTION

It has been found that a fraction enriched with stearidonic acid having a purity of more than 90% by weight can be prepared from a mixture of fatty acids in which it is present without any need for molecular distillation of the ethyl esters and with only one chromatographic operation.

Accordingly, the invention relates to a process for the production of stearidonic acid in which a mixture of fatty acids containing this acid is reacted with urea a fraction enriched with polyunsaturated fatty acids is collected, and the enriched fraction is injected into a high-performance reverse-phase liquid chromatography column and is eluted from this column.

The process according to the invention is characterized in that a mixture of 75 to 95% by weight methanol for 25 to 5% by weight water is used as eluent and the fatty acids are injected into the column in the form of a 25 to 35% by weight solution.

DETAILED DESCRIPTION OF THE INVENTION

A starting oil containing a perceptible percentage of stearidonic acid, of the order of 2 to 4%, is preferably used for carrying out the process according to the invention. Fish oil and particularly blackcurrant seed oil (Ribes nigrum) are suitable in this regard.

Fish oil contains useful proportions of stearidonic acid, eicosapentaenoic acid (EPA, C 20:5 Δ5,8,11,14,17) and docosahexaenoic acid (DHA, C22:6 Δ4,7,10,13,16,19) while blackcurrant seed oil is an important source of γ-linolenic and stearidonic acids.

The crude oils extracted, for example by solvent or by pressure, are first refined by degumming in known manner, for example with phosphoric acid, neutralization of the free fatty acids, for example with sodium hydroxide, decoloration, for example with a mixture of active carbon and activated aluminium silicate, deodorization in vacuo at a temperature of approximately 200° C. in the case of black-currant seed oil and, optionally, winterizing by cooling, for example to approximately 4.C for about 24 hours, which enables most of the residual waxes to be eliminated in the case of blackcurrant seed oil.

Fish oil is refined in the same way as blackcurrant seed oil, except that the deodorizing step is preferably carried out at a temperature of $\leq 180°$ C. to avoid degradation of the polyunsaturated fatty acids. The starting mixture of free fatty acids is obtained by saponification of the refined or semi-refined oils and acidification of the fatty acid salts obtained or even by hydrolysis of the refined or semi-refined oils. Semi-refining comprises degumming and neutralization of the crude oils.

The fatty acid mixture is then treated with urea in a ratio by weight of fatty acids to urea of 1:3 to 1:6 and preferably 1:3 to 1:4 in the presence of methanol in a ratio by weight of urea to methanol of 1:1.5 to 1:3 and preferably 1:2.1 by heating the mixture to the boiling temperature. The reaction mixture is then cooled to a temperature of $-5°$ to 20° C. and preferably 0° to 15° C., after which the cooled mixture is left standing at the final temperature for at most 15 hours and preferably for 1 to 7 hours. The precipitate formed is then cold-filtered, the liquid phase is recovered and the fatty acid mixture enriched with polyunsaturates is extracted therefrom, for example in a hydrochloric medium in the presence of hexane, the hexane being subsequently eliminated.

The following step comprises fractionation of the fatty acid mixture enriched with polyunsaturates by high-performance reversed-phase liquid chromatography. This type of preparative chromatography comprises injecting the fatty acids into the apparatus in the form of samples, adsorbing them through their hydrophobic part onto a column (constituting the stationary phase) of porous silica doped with a layer of saturated hydrocarbons and then selectively desorbing them by a mobile phase of controlled polarity in which the polar parts of the samples are dissolved and which constitutes the eluent.

In the present case, the eluent consists of a water/methanol mixture preferably containing 85 to 90% by weight methanol for 15 to 10% by weight water. The mobile phase represents 1 to 3 g per liter adsorbent in the column and preferably 1.5 to 2 g/l.

The fatty acids are preferably present in the injection sample in the form of a solution in a good solvent for the fatty acids, for example methanol. The concentration of the fatty acids in the injection sample is a factor determining the success of the separation. It is preferably of the order of 30% by weight for approximately 70% by weight methanol.

It has in fact been found that better separation of the stearidonic acid is achieved with a more concentrated solution of fatty acids than in the case of state-of-the-art separation by chromatography. The effect of concentration in this regard is unexpected in the sense that separation could be expected to be facilitated by dilution. The remarkable result of the process according to the invention is due primarily to the suitable choice of the composition of the eluent and of the fatty acid concentration of the mobile phase.

The invention also relates to the use of the stearidonic acid obtained by the process according to the invention for the production of a pharmaceutical composition against the cardiovascular and thrombo-embolic diseases associated with platelet aggregation.

The pharmaceutical composition in question may be formulated in unit dosage forms according to the method of administration, for example oral, enteral, rectal or parenteral. For example, it may be made up in the form of capsules, gelatin-coated tablets, suppositories or syrups. In the case of enteral or parenteral administration, the compositions are formulated as chemically and physically stabilized, apyrogenic and sterile solutions or emulsions.

The stearidonic acid may advantageously be protected against oxidation by a suitable antioxidant, for example ascorbyl palmitate, tocopherols, a mixture of such anti-oxidants or a mixture of ascorbic acid, tocopherol and lecithin.

The dose administered depends on the type and seriousness of the condition to be treated. It may be from 0.1 to 1 g stearidonic acid per day in a single dose or, preferably, in 2 to 3 separate doses.

The invention is illustrated by the following Examples in which parts and percentages are by weight, unless otherwise indicated.

EXAMPLES

In the following Examples, the fatty acids were analyzed by gas phase chromatography of their methyl esters.

EXAMPLE 1

A solution of 30.5 parts sodium hydroxide in a mixture of 101.5 parts water and 80.5 parts ethanol is added with thorough stirring to 100 parts refined blackcurrant seed oil and the mixture is heated for 30 minutes to the boiling temperature (approximately 80° C.). The mixture is then cooled to 30°–40° C. and 100 parts 32% hydrochloric acid (pH 1) and 166.7 parts hexane are slowly added with vigorous stirring over a period of 30 minutes. The mixture is then decanted. Two phases are formed. The upper phase is removed and the hexane is evaporated therefrom in vacuo at 40° C. The resulting mixture constitutes the starting fatty acid mixture. This mixture consists of the following fatty acids:

|   | % |
|---|---|
| C 16:0 | 7 |
| C 18:0 | 1.3 |
| C 18:1 cis | 11.7 |
| C 18:2 Δ9,12 | 47.3 |

-continued

|   | % |
|---|---|
| C 18:3 Δ6,9,12 | 16.4 |
| C 18:3 Δ9,12,15 | 13.8 |
| C 18:4 Δ6,9,12,15 (SA) | 2.5 |

450 g urea and 945 g methanol are added to 150 g of the above fatty acid mixture which is then heated to the boiling temperature at which it becomes clear. It is then left to cool to ambient temperature and is then placed in a water bath at 0° C. for 5 h. A precipitate is formed. The liquid phase is then recovered by vacuum filtration in a Buchner cooled beforehand to 0° C., after which the fatty acids enriched with polyunsaturates are extracted with 0.2 pat hydrochloric acid, 0.6 part water and 0.25 part hexane for 1 part liquid phase. Finally, the hexane is evaporated in vacuo at 40° C. and a fatty acid mixture o the following composition is collected:

|   | % |
|---|---|
| C 18:2 Δ6,9 | 2.1 |
| C 18:3 Δ6,9,12 | 80.7 |
| C 18:3 Δ9,12,15 | 2.1 |
| C 18:4 Δ6,9,12,15 (SA) | 15.1 |

Chromatography is carried out using two columns with an internal diameter of 5.7 cm and a length of 30 cm arranged in series and filled with porous silica doped with saturated $C_{18}$ hydrocarbons constituting the stationary phase. The columns are under 30 bar nitrogen pressure (radial compression) and are equipped with a preferential refractive index detector for quantitative identification of the fractions. The mobile phase consists of a methanol: water mixture containing approximately 12% water with a density of 0.821 to 0.824.

10 ml samples of a solution of 30% of the fatty acid mixture in 70% methanol are injected so that they are adsorbed onto the column. The various fractions are then eluted by passing the mobile phase through the column at a rate of 100 ml/minute. Several fractions are collected, and the fraction relating to the first peak is set aside. It corresponds to 10% of the fatty acid mixture introduced into the apparatus and contains 92% stearidonic acid. The yield of 92% pure stearidonic acid thus rises to 1.5% of the starting fatty acid mixture, which corresponds to 56% of the stearidonic acid present in the starting material.

EXAMPLE 2

The fraction obtained in Example 1 is reinjected as 10 ml samples of a 30% solution in methanol under the same conditions. The fraction relating to the first peak is collected; it corresponds to 60% of the fatty acid mixture reinjected and contains 98% stearidonic acid.

EXAMPLE 3

The procedure is as in Example 1, starting with a mixture of fish oil fatty acids fractionated with urea under the same conditions apart from the final standing temperature of the complex mixture with urea/liquid phase, which is 10° C. The mixture of fatty acids has the following composition:

|   | % |
|---|---|
| C 18:4 Δ6,9,12,15 (SA) | 16.3 |

-continued

|  | % |
|---|---|
| C 20:5 Δ5,8,11,14,17 (EPA) | 34.9 |
| C 22:6 Δ4,7,10,13,16,19 (DHA) | 38.6 |
| Others | 10.2 |

The chromatography is carried out in the same way as in Example 1 in regard to the composition of the mobile phase and the elution rate. The only change is the specific charge of starting fatty acids of 1.75 g/l adsorbent in the column. Several fractions are collected and the fraction relating to the second peak, which has the following fatty acid composition, is set aside:

|  | % |
|---|---|
| C 18:3 Δ9,12,15 (ALA) | 5 |
| C 18:4 Δ6,9,12,15 (SA) | 86 |
| Others | 9 |

This fraction represents 0.9% of the starting fatty acid mixture, which corresponds to 35% of the stearidonic acid present in the starting material.

EXAMPLE 4

It is accepted that cardiovascular and thrombo-embolic diseases are often associated with hyperactivity of the blood platelets. Polyunsaturated fatty acids of the n-3 series are considered to be prevention factors against thrombo-embolic disease.

The stearidonic acid obtained in accordance with Example 2 is studied for its effect on platelet aggregation by comparison with γ-linolenic acid, α-linolenic acid and eicosapentaenoic acid and by comparison with the fatty acid mixture obtained in accordance with Example 2 of EP 178 442 (referred to hereinafter as concentrate).

The blood of blood donors with an average age of 36 years is collected, an anticoagulant is added and the platelets are isolated. The platelets are then suspended in a Tyrode HEPES solution of pH 7.35 which is kept for 16 h at 37° C. in tubes closed under nitrogen and containing:

50 μM delipidized human albimin
50 μM linoleic acid (LA, C 18:2 Δ9,12)
5 μM arachidonic acid (AA, C 20:4 Δ5,8,11,14)
and 5 μM of the studied fatty acid.

The platelets are incubated in this solution for 2 h at 37° C., re-isolated and then taken up in a Tyrode HEPES solution to which 0.1% gelatin is added. For each test, a batch of platelet suspension serving as control is subjected to the same treatment except that the suspension contains only linoleic and arachidonic acid of which the presence does not affect the platelet functions. In certain tests, 10 μM α-tocopherol is added in addition to the various fatty acids to compensate for the depletion of this compound caused by the polyunsaturated fatty acids. The platelets thus enriched are under conditions similar to those prevailing in blood plasma.

Platelet aggregation is measured by Born's turbidimetric method (J. Physiol. 209:487, 1973).

The concentration of the aggregating agent is calculated to obtain approximately 60% aggregation 4 minutes after the addition of the aggregating agent with the platelets in question as control.

The results are shown in Table 1 below expressed as % aggregation and represent a mean the standard deviation in each case in parallel with the control.

TABLE 1

| Fatty acid added | Aggregating agent | | | |
|---|---|---|---|---|
|  | Collagen | Arachidonic acid | Analog of PGH 2 (U 46619) | Thrombin |
| SA | 47 ± 12 | 30 ± 6 | 51 ± 15 | 53 ± 12 |
| Control | 58 ± 8 | 47 ± 5 | 63 ± 3 | 62 ± 7 |
| GLA | 51 ± 12 | — | 47 ± 11 | 57 ± 15 |
| Control | 60 ± 9 | — | 62 ± 11 | 59 ± 6 |
| ALA | 47 ± 12 | — | 50 ± 9 | 54 ± 3 |
| Control | 58 ± 9 | — | 56 ± 7 | 61 ± 10 |
| EPA | 46 ± 12 | — | 45 ± 13 | 59 ± 13 |
| Control | 60 ± 9 | — | 62 ± 11 | 59 ± 8 |
| Concentrate | 50 ± 9 | — | 57 ± 13 | 61 ± 8 |
| Control | 58 ± 9 | — | 57 ± 6 | 61 ± 10 |

Legend: — = not tested

The above results show that SA inhibits the platelet aggregation induced by collagen, arachidonic acid, the PGH2 analog or thrombin. Compared with GLA, ALA and EPA, SA inhibits the stimulation by thrombin more specifically. In addition, it was found that the presence f 10 μM α-tocopherol did not affect platelet aggregation.

We claim:

1. A process for obtaining stearidonic acid from a mixture of fatty acids comprising reacting a mixture of fatty acids containing stearidonic acid with urea and collecting a fraction enriched with polyunsaturated fatty acids, preparing a 25% to 35% by weight solution of fatty acids obtained from the fraction in a solvent, injecting a sample of the solution into a high-performance reverse-phase liquid chromatography column having a porous silica stationary phase adsorbent doped with a layer of saturated hydrocarbons, passing a mobile phase of 75% to 95% by weight methanol and 25% to 5% by weight water through the column, and collecting a fraction containing stearidonic acid.

2. A process according to claim 1 wherein the mobile phase comprises 85% to 90% by weight methanol and 15% to 10% by weight water.

3. A process according to claim 1 wherein there is 1 to 3 grams mobile phase per liter of stationary phase adsorbent in the column.

4. A process according to claim 1 wherein there is 1.5 to 2 grams mobile phase per liter of stationary phase adsorbent in the column.

5. A process according to claim 1 wherein the solvent is methanol.

6. A process according to claim 1 further comprising injecting the collected fraction containing stearidonic acid into the column, passing the mobile phase through the column, and collecting a second fraction enriched in stearidonic acid.

7. A process according to claim 1 wherein the mixture of fatty acids reacted with urea is obtained form blackcurrant seed oil.

8. A process according to claim 1 wherein the mixture of fatty acids reacted with urea is obtained from fish oil.

9. A pharmaceutical composition in unit dosage form comprising a fatty acid fraction comprised of stearidonic acid in an amount of more than 90% by weight of the fraction.

10. A pharmaceutical composition according to claim 9 in a form suitable for oral administration.

11. A pharmaceutical composition according to claim 9 in a form suitable for rectal administration.

12. A pharmaceutical composition according to claim 9 in a form suitable for general administration.

13. A pharmaceutical composition according to claim 9 in a form suitable for parenteral administration.

14. A pharmaceutical composition according to claim 9 further comprising an antioxidant selected from the group consisting of ascorbyl palmitate, tocopherols, and mixtures thereof.

15. A pharmaceutical composition according to claim 9 further comprising an antioxidant mixture comprising ascorbic acid, tocopherol and lecithin.

16. A method for treating cardiovascular and thrombo-embolic diseases associated with platelet aggregation comprising administering 0.1 g to 1 g stearidonic acid per day in unit dosage form.

17. A method according to claim 16 wherein the stearidonic acid is a fatty acid fraction comprised of stearidonic acid in an amount of more than 90% by weight of the fraction.

18. A method according to claim 16 wherein the pharmaceutical composition is in a form suitable for oral administration.

19. A method according to claim 16 wherein the pharmaceutical composition is in a form suitable for rectal administration.

20. A method according to claim 16 wherein the pharmaceutical composition is in a form suitable for enteral or parenteral administration.

* * * * *

UNITED STATES PATENT AND TRADEMARK OFFICE
CERTIFICATE OF CORRECTION

PATENT NO. : 5,130,449
DATED : July 14, 1992
INVENTOR(S) : Michel Lagarde, et. al.

It is certified that error appears in the above-indentified patent and that said Letters Patent is hereby corrected as shown below:

On the Title page, item [57], Abstract, line 3, "at" should be --a--.

Column 1, line 59, after "urea", insert a comma.

Column 7, line 4, "general" should be --enteral--.

Signed and Sealed this

Seventeenth Day of August, 1993

Attest:

BRUCE LEHMAN

*Attesting Officer*     *Commissioner of Patents and Trademarks*